United States Patent
Kitamoto et al.

(10) Patent No.: US 10,241,049 B2
(45) Date of Patent: Mar. 26, 2019

(54) OPTICAL FIBER FLUORESCENCE DETECTION DEVICE

(71) Applicant: Enplas Corporation, Saitama (JP)

(72) Inventors: Ken Kitamoto, Saitama (JP); Koichi Ono, Saitama (JP)

(73) Assignee: ENPLAS CORPORATION, Saitama (JP)

( * ) Notice: Subject to any disclaimer, the term of this patent is extended or adjusted under 35 U.S.C. 154(b) by 85 days.

(21) Appl. No.: 15/120,025

(22) PCT Filed: Feb. 16, 2015

(86) PCT No.: PCT/JP2015/054147
§ 371 (c)(1),
(2) Date: Aug. 18, 2016

(87) PCT Pub. No.: WO2015/125735
PCT Pub. Date: Aug. 27, 2015

(65) Prior Publication Data
US 2017/0059484 A1 Mar. 2, 2017

(30) Foreign Application Priority Data

Feb. 19, 2014 (JP) ................................ 2014-029475

(51) Int. Cl.
*G01N 21/64* (2006.01)
*G01N 21/05* (2006.01)
*G01N 33/02* (2006.01)

(52) U.S. Cl.
CPC ........... *G01N 21/645* (2013.01); *G01N 21/05* (2013.01); *G01N 21/6428* (2013.01);
(Continued)

(58) Field of Classification Search
CPC .. G01N 21/645; G01N 21/05; G01N 21/6428; G01N 33/02; G01N 2021/6439; G01N 2021/6482; G01N 2021/648
(Continued)

(56) References Cited

U.S. PATENT DOCUMENTS 5,449,625 A * 9/1995 Kobayashi ......... G01N 33/5302
250/458.1
2005/0018264 A1 1/2005 Benedict
(Continued)

FOREIGN PATENT DOCUMENTS

EP 2352035 A1 8/2011
JP 2000-293881 A 10/2000
(Continued)

OTHER PUBLICATIONS

Wang, Ling et al., 2007, "Optical probe based on double-clad optical fiber for fluorescence spectroscopy", Optics Express, 15 (26), pp. 17681-17689.*
(Continued)

*Primary Examiner* — David Porta
*Assistant Examiner* — Blake Riddick
(74) *Attorney, Agent, or Firm* — Brundidge & Stanger, P.C.

(57) ABSTRACT

This detection device is provided with: a chip including a detection region for detecting a substance to be detected; a light source which emits excitation light; a detector for detecting the fluorescence emitted from a fluorescent substance which labels the substance to be detected, and which is excited by the excitation light; and an optical fiber which includes a core, and a cladding covering the outer peripheral surface of the core, guides, to the detection region, the excitation light emitted from the light source, and guides, to the detector, the fluorescence emitted from the fluorescent
(Continued)

substance. The optical fiber is fixed to the chip directly or via a connector. The excitation light emitted from the light source is guided within the core, and reaches the detection region of the chip. The fluorescence emitted from the fluorescent substance is guided within the core and the cladding, and reaches the detector.

7 Claims, 9 Drawing Sheets

(52) U.S. Cl.
CPC ..... *G01N 33/02* (2013.01); *G01N 2021/6439* (2013.01); *G01N 2021/6482* (2013.01); *G01N 2021/6484* (2013.01)

(58) Field of Classification Search
USPC ............................... 250/458.1, 459.1, 227.11
See application file for complete search history.

(56) References Cited

U.S. PATENT DOCUMENTS

| | | | |
|---|---|---|---|
| 2005/0140971 A1* | 6/2005 | Yamaguchi | B01L 3/502715 356/246 |
| 2005/0175273 A1 | 8/2005 | Iida et al. | |
| 2009/0003789 A1 | 1/2009 | Bouma | |
| 2010/0224793 A1* | 9/2010 | Fukuzawa | G01N 21/645 250/458.1 |
| 2010/0247043 A1* | 9/2010 | Sugawara | G02B 6/4201 385/93 |
| 2011/0134420 A1* | 6/2011 | Matsumoto | B01L 3/502715 356/246 |
| 2012/0075623 A1 | 3/2012 | Matsumoto et al. | |
| 2014/0147930 A1* | 5/2014 | Orwar | B01L 3/022 436/174 |

FOREIGN PATENT DOCUMENTS

| | | |
|---|---|---|
| JP | 2003-302360 A | 10/2003 |
| JP | 2004-069395 A | 3/2004 |
| JP | 2004-077305 A | 3/2004 |
| JP | 2009-063601 A | 3/2009 |
| JP | 2010-043983 A | 2/2010 |
| JP | 2012-093350 A | 5/2012 |
| WO | 2010/010904 A1 | 1/2010 |

OTHER PUBLICATIONS

Ling Wang et al "Optical probe based on double-clad optical fiber for fluorescence spectroscopy References and links", Optics Express, vol. 15, No. 26, pp. 17681-17689, XP055391734, Dec. 24, 2007.
Extended European Search Report for 15751797.0 dated Jul. 26, 2017.
International Search Report from International Application No. PCT/JP2015/054147 dated May 19, 2015.

* cited by examiner

OPTICAL FIBER FLUORESCENCE DETECTION DEVICE

TECHNICAL FIELD

The present invention relates to a detection apparatus which detects a detection object substance by detecting fluorescence emitted from a fluorescence material labelling the detection object substance.

BACKGROUND ART

In recent years, in the field of food tests, laboratory tests, environment tests and the like, analysis of trace detection object substances such as protein and nucleic acid is performed. For detection of these detection object substances, detection apparatuses which can quantitatively detect the detection object substances with high sensitivity are used.

A known example of the detection apparatuses which can detect a detection object substance with high sensitivity is an apparatus which utilizes fluorescence emitted from a fluorescence material labelling a detection object substance (see, for example, PTL 1).

The detection apparatus disclosed in PTL 1 includes a light source section, a chip and a detection section. The light source section is disposed above the chip, and the detection section is disposed below the chip with a space therebetween.

The light source section includes an optical fiber, a rod lens disposed at one end portion of the optical fiber, and a light source which is optically connected with the other of end portion of the optical fiber and configured to emit excitation light. In addition, the chip includes a channel in which a capturing body capturing a detection object substance labeled by a fluorescence material is disposed. In addition, the chip does not allow excitation light to pass therethrough. The detection section includes a sensor and a computer connected with the sensor.

In the detection apparatus disclosed in PTL 1, excitation light sent by the optical fiber is applied toward the chip (fluorescence material) through the rod lens. The fluorescence material irradiated with the excitation light is excited, and emits fluorescence. At this time, the chip does not allow the excitation light to pass therethrough, and thus only fluorescence reaches the sensor.

CITATION LIST

Patent Literature

PTL 1
Japanese Patent Application Laid-Open No. 2003-302360

SUMMARY OF INVENTION

Technical Problem

However, in the detection apparatus disclosed in PTL 1, the sensor for detecting radially emitted fluorescence is disposed below the chip with a space therebetween. Consequently, disadvantageously, fluorescence emitted in directions other than the direction of the detection section cannot be detected, and sufficient detection sensitivity cannot be obtained. In addition, since the optical fiber and the sensor are separated from the chip with a space therebetween, optical axis alignment at the time when excitation light is emitted toward the chip (fluorescence material) is difficult. When the optical axis alignment cannot be appropriately performed, disadvantageously, sufficient detection sensitivity cannot be obtained.

In view of this, an object of the present invention is to provide a detection apparatus which can detect fluorescence emitted from a fluorescence material with high sensitivity and can readily perform optical axis alignment.

Solution to Problem

A detection apparatus according to embodiments of the present invention includes: a chip including a detection target region for detecting a detection object substance; a light source configured to emit excitation light; a detector configured to detect fluorescence emitted from a fluorescence material labelling the detection object substance and excited with the excitation light; and an optical fiber including a core and a clad which covers an outer peripheral surface of the core, the optical fiber being configured to guide excitation light emitted from the light source to the detection target region, and guide fluorescence emitted from the fluorescence material to the detector. The optical fiber is directly fixed to the chip, or fixed to the chip through a connector; the excitation light emitted from the light source is guided in the core and reaches the detection target region of the chip; and the fluorescence emitted from the fluorescence material is guided in the core and the clad and reaches the detector.

Advantageous Effects of Invention

The detection apparatus of the present invention can detect fluorescence with high sensitivity without performing complicated optical axis alignment, and thus can readily detect a detection object substance with high sensitivity.

DESCRIPTION OF EMBODIMENTS

In the following, embodiments of the present invention will be described in detail with reference to the accompanying drawings.

[Embodiment 1]
(Configuration of Detection Apparatus)

The detection apparatus according to an embodiment of the present invention is an apparatus for detecting a detection object substance by irradiating a fluorescence material labelling a detection object substance in a detection target region of a chip with excitation light, and detecting fluorescence emitted from the detection target region (fluorescence material).

Figure 1:
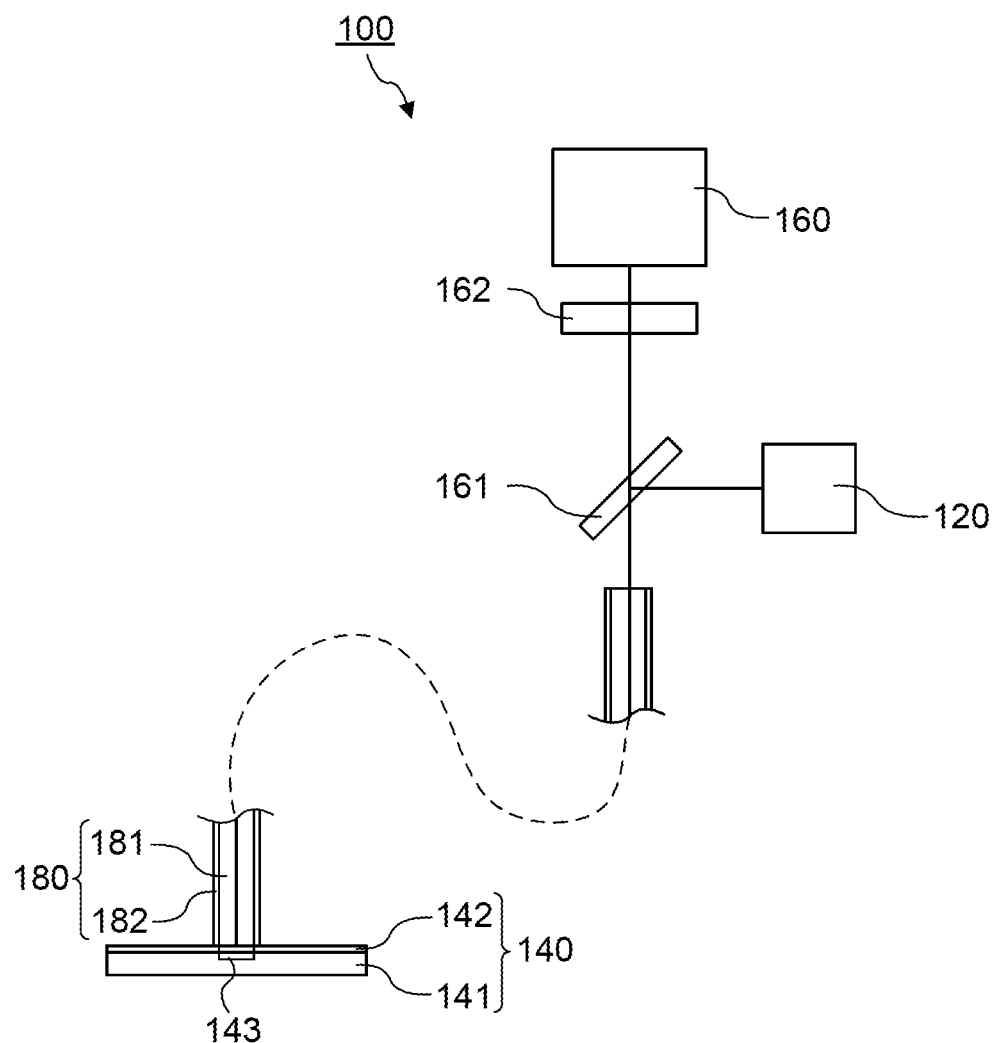
FIG. 1 illustrates a configuration of a detection apparatus according to Embodiment 1.

FIG. 1 illustrates a configuration of detection apparatus 100 according to Embodiment 1 of the present invention. As illustrated in FIG. 1, detection apparatus 100 includes chip 140 including detection target region 149 for detecting a detection object substance, light source 120 configured to emit excitation light, detector 160 configured to detect fluorescence emitted from a fluorescence material which labels a detection object substance and is excited with excitation light, optical fiber 180 configured to guide excitation light emitted from light source 120 to detection target region 149 and guide fluorescence emitted from the fluorescence material to detector 160, dichroic mirror 161 configured to reflect the excitation light emitted from light source 120 toward an end surface of optical fiber 180, and filter 162 configured to adjust the intensity of fluorescence.

Light source 120 emits excitation light for causing emission of fluorescence from a fluorescence material. The type of the light source is not limited, and may be appropriately selected in accordance with the type of the fluorescence material to be used and the like. Light source 120 is, for example, a mercury lamp, a xenon lamp, an LED, a laser or the like. In addition, light source 120 may include a filter which allows predetermined excitation light to pass therethrough.

Detector 160 detects the fluorescence emitted from the fluorescence material. The type of detector 160 is not limited as long as the fluorescence can be detected. Examples of detector 160 include a charge-coupled device (CCD), a photomultiplier tube (PMT) and the like.

Dichroic mirror 161 reflects the excitation light emitted from light source 120 toward an end surface of optical fiber 180. In addition, dichroic mirror 161 allows the fluorescence emitted from the end surface of optical fiber 180 to pass therethrough.

Filter 162 blocks light having a wavelength other than that of the fluorescence which is incident on detector 160. Filter 162 is disposed between dichroic mirror 161 and detector 160. The fluorescence having passed through dichroic mirror 161 is adjusted by filter 162, and reaches detector 160.

On the light path of the excitation light from light source 120 to chip 140, dichroic mirror 161 and optical fiber 180 are disposed in this order from light source 120 side. The excitation light emitted from light source 120 is reflected at dichroic mirror 161 toward an end surface of optical fiber 180. The excitation light reflected by dichroic mirror 161 is applied to a detection target region (fluorescence material) of chip 140 through optical fiber 180. In addition, on the light path of the fluorescence from chip 140 to detector 160, optical fiber 180, dichroic mirror 161 and filter 162 are disposed in this order from chip 140 side. The excitation light emitted from the fluorescence material (detection target region) passes through optical fiber 180, dichroic mirror 161 and filter 162, and reaches detector 160.

Figure 2A:
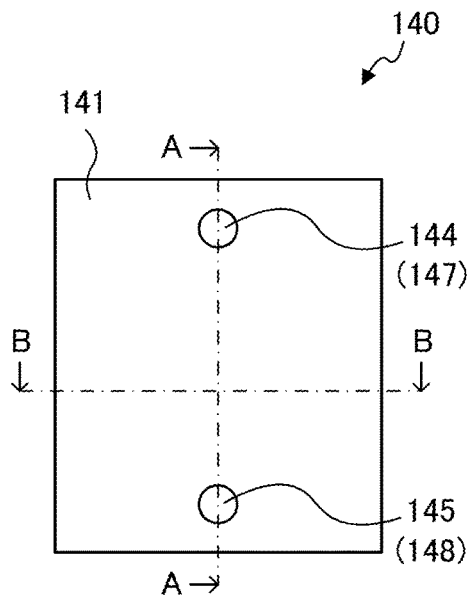
FIG. 2A to FIG. 2D illustrate a configuration of chip.
Figure 2B:
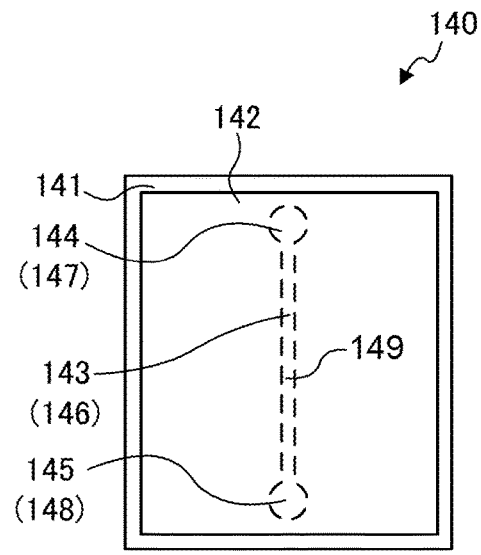
Figure 2C:
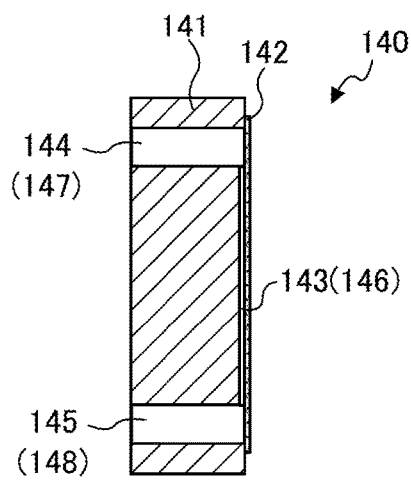
Figure 2D:
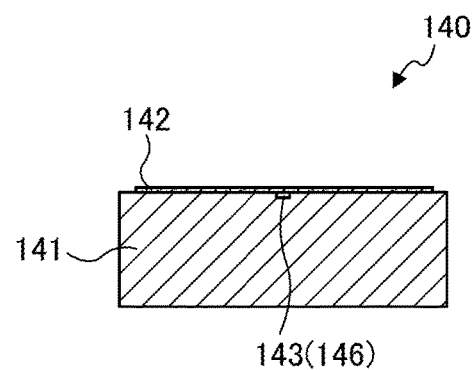

FIG. 2A to FIG. 2D illustrate a configuration of chip 140. FIG. 2A is a plan view of chip 140, FIG. 2B is a bottom view of chip 140, FIG. 2C is a sectional view taken along line A-A of FIG. 2A, and FIG. 2D is a sectional view taken along line B-B of FIG. 2A.

As illustrated in FIG. 2, chip 140 is a device for flowing of a liquid sample. Chip 140 is composed of substrate 141 and film 142. Chip 140 includes channel 143, sample inlet 144, sample outlet 145 and detection target region 149. One end of channel 143 is communicated with sample inlet 144. In addition, the other end of channel 143 is communicated with sample outlet 145. The number and installation position of channel 143 are not limited. In the present embodiment, one channel 143 is disposed. In addition, in the present embodiment, one sample inlet 144 and one sample outlet 145 are disposed. The cross-sectional area and the cross-sectional shape of the channel in the direction orthogonal to the direction of liquid flow are not limited. A sample introduced from sample inlet 144 flows to sample outlet 145 through channel 143.

Detection target region 149 is a region of an internal surface of channel 143, and, in the present embodiment, is a region where a capturing body for capturing a detection object substance is fixed. The capturing body is disposed at a part of the bottom surface of channel 143. The region where capturing body is disposed is detection target region 149. A detection object substance in a sample introduced from sample inlet 144 is captured by the capturing body fixed in detection target region 149 of channel 143. It is to be noted that a capturing body may not be disposed in detection target region 149. That is, it is also possible to adopt a configuration in which the detection object substance labeled with the fluorescence material is detected in detection target region 149 in the course of flowing in channel 143.

Substrate 141 is a flat plate made of a resin including groove 146, first through hole 147 and second through hole 148. One end of groove 146 is communicated with first through hole 147. In addition, the other end of groove 146 is communicated with second through hole 148. When one opening part of first through hole 147, an opening part of groove 146, and one opening part of second through hole 148 are sealed with film 142, sample inlet 144, channel 143 and sample outlet 145 are formed. The type of the resin of substrate 141 is not limited as long as channel 143 can be formed together with film 142, and may be appropriately selected from publicly known resins. The examples of the resin of substrate 141 include polyethylene terephthalate, polycarbonate, polymethylmethacrylate, vinyl chloride, polypropylene, polyether, polyethylene, polystyrene, silicone resin and the like.

Film 142 is a substantially rectangular transparent resin film. Film 142 is bonded on one surface of substrate 141 on which groove 146 is opened. The way of bonding substrate 141 and film 142 is not limited, and substrate 141 and film 142 may be bonded by thermo compression bonding, for example. The type of the resin of film 142 is not limited as long as channel 143 can be formed together with substrate 141, and the excitation light and the fluorescence can pass therethrough. Preferably, the thickness of film 142 is small as much as possible in consideration of the type (rigidity) of the resin, the bonding property of film 142 and the like. When film 142 having a large thickness is used, absorption of detection light (fluorescence) in detection target region 149 is increased, and a desired signal intensity cannot be obtained. In the present embodiment, film 142 has a thickness of about 20 μm.

Figure 3A:
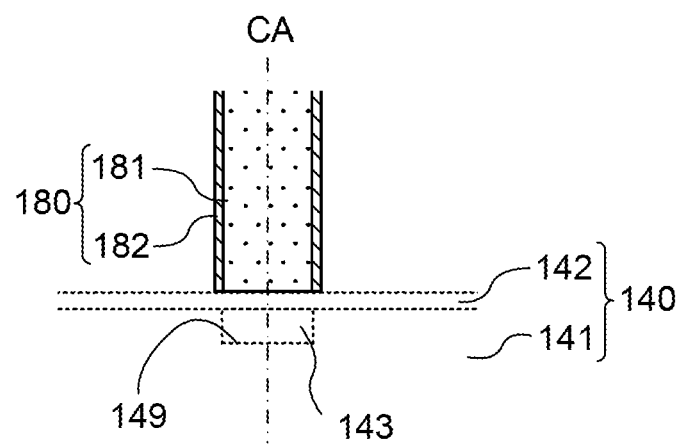
FIG. 3A and FIG. 3B illustrate a positional relationship between an optical fiber and a chip.
Figure 3B:
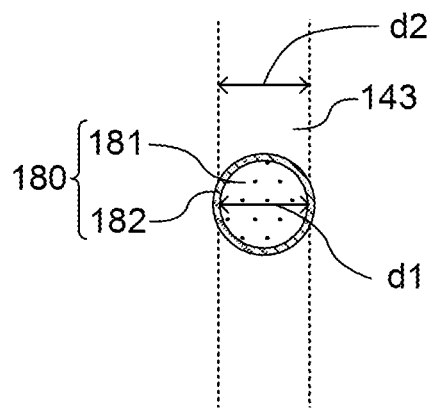
Figure 4A:
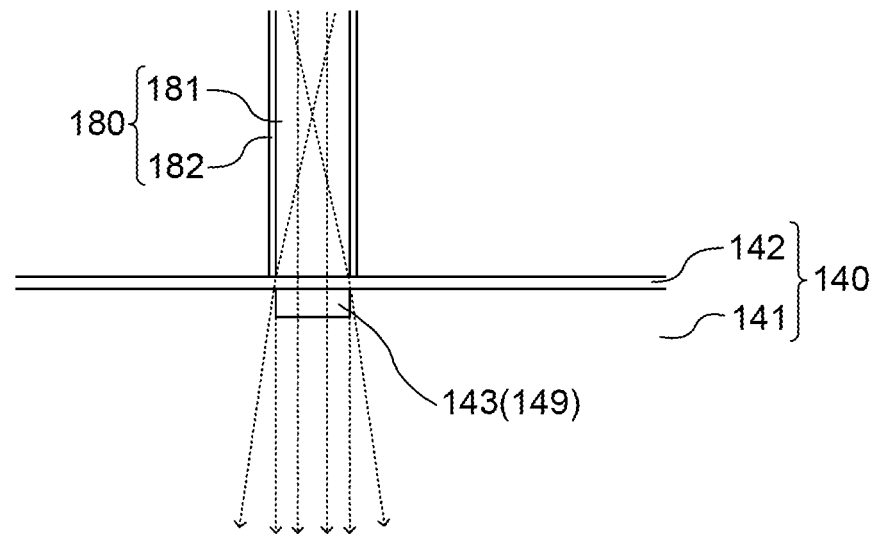
FIG. 4A illustrates a part of light paths of excitation light in the optical fiber part and FIG. 4B illustrates a part of light paths of fluorescence in the optical fiber part.
Figure 4B:
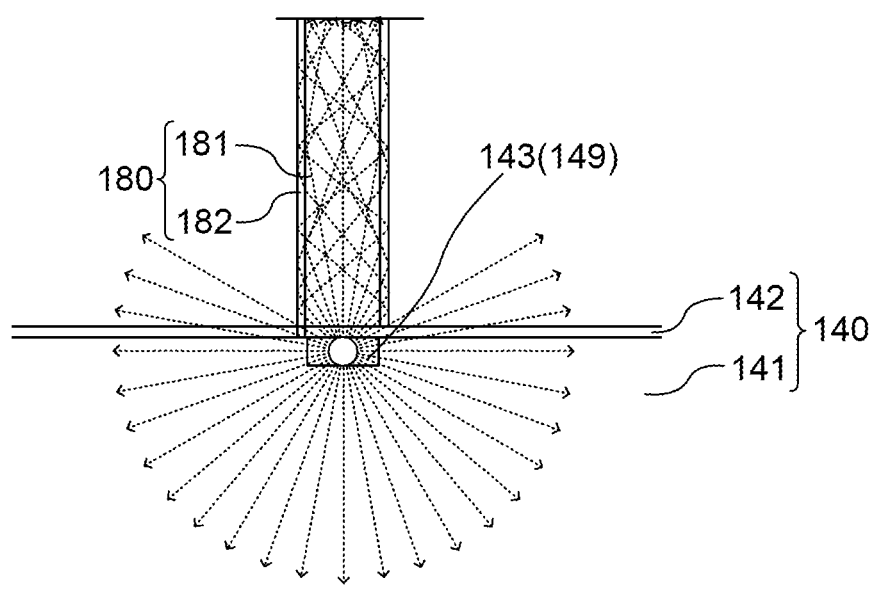

FIG. 3A and FIG. 3B illustrate a positional relationship between optical fiber 180 and chip 140. FIG. 3A is a sectional view of optical fiber 180 and chip 140 along central axis CA of optical fiber 180 in the width direction of channel 143, and FIG. 3B is a sectional view of optical fiber 180 in a direction orthogonal to central axis CA of optical fiber 180. It is to be noted that, in FIG. 3A and FIG. 3B, substrate 141, film 142 and channel 143 are illustrated with broken lines. FIG. 4A and FIG. 4B illustrate light paths of optical fiber 180 in detection apparatus 100. FIG. 4A illustrates a part of the light paths of excitation light, and FIG. 4B illustrates a part of light paths of fluorescence.

As illustrated in FIG. 4A and FIG. 4B, optical fiber 180 guides the excitation light emitted from light source 120 to detection target region 149 (fluorescence material), and guides the fluorescence emitted from the fluorescence material toward detector 160. Optical fiber 180 is an optical transmission cable including core 181 and clad 182. Preferably, one end portion of optical fiber 180 is in contact with the surface (film 142) of chip 140. With this configuration, the fluorescence emitted from the fluorescence material can be efficiently guided toward detector 160, and the excitation light emitted from light source 120 can be efficiently applied to detection target region 149 (fluorescence material).

Core 181 guides the excitation light emitted from light source 120 and reflected by dichroic mirror 161 to the fluorescence material of detection target region 149, and guides the fluorescence emitted from the fluorescence material toward detector 160. Core 181 is disposed along central axis CA of optical fiber 180. In the direction orthogonal to central axis CA, core 181 has a circular cross-sectional shape. In addition, preferably, in the direction orthogonal to central axis CA, diameter d1 of core 181 is approximately equal to width d2 (detection target region) of channel 143 (see FIG. 3A and FIG. 3B). When diameter d1 of core 181 in the direction orthogonal to central axis CA is significantly small in comparison with width d2 of channel 143, the irradiation area of the excitation light applied to a fluorescence material is small, and consequently the excitation light cannot be uniformly applied. It should be noted that the excitation light emitted from an end portion of optical fiber 180 has a spread angle in accordance with the numerical aperture (NA) of optical fiber 180 during the emission. Accordingly, diameter d1 of core 181 in the direction orthogonal to central axis CA may be set to a value slightly smaller than width d2 of channel 143 in accordance with the distance from an end portion of core 181 to detection target region 149. On the other hand, when diameter d1 of core 181 in the direction orthogonal to central axis CA is significantly larger than width d2 of channel 143, the excitation light which is not applied to the fluorescence material in the excitation light emitted from light source 120 is wasted. It should be noted that for allowance of an error in accordance with the accuracy of the optical axis alignment, a value slightly larger than width d2 of channel 143 may be set. In this manner, diameter d1 of core 181 in the direction orthogonal to central axis CA is set in accordance with width d2 (detection target region) of channel 143. In the present embodiment, in the direction orthogonal to central axis CA, core 181 has a diameter of about 105 µm with respect to channel 143 having a width of 100 µm. Preferably, with respect to the width of channel 143, the diameter of core 181 is set to ±10%, and to about ±10 µm in the absolute value. The material of core 181 is not limited as long as the excitation light and the excitation light can pass therethrough. Examples of the material of core 181 include quartz, multicomponent glass, polymethyl methacrylate (PMMA) and the like.

Clad 182 is disposed on the outside of core 181 in such a manner as to cover the outer peripheral surface of core 181. The outer diameter of clad 182 in the direction orthogonal to central axis CA is not limited. The outer diameter of clad 182 in the direction orthogonal to central axis CA is about 100 µm to 2 mm That is, the thickness of clad 182 in the direction orthogonal to central axis CA is about 25 to 975 µm. The kind of the material of the clad is not limited as long as the excitation light can pass therethrough. Examples of the material of clad 182 include quartz, multicomponent glass, silicone resin and the like. In particular, preferably, the material of clad 182 has a refractive index lower than that of core 181, and has a refractive index higher than that of the environment adjacent to the outer periphery of clad 182, in view of guiding fluorescence emitted from the fluorescence material to detector 160.

As illustrated in FIG. 4A, the excitation light emitted from light source 120 is reflected by dichroic mirror 161, and emitted toward chip 140 (fluorescence material) through core 181. The excitation light emitted toward chip 140 passes through film 142, and is applied to a fluorescence material disposed in detection target region 149. As illustrated in FIG. 4B, in the fluorescence emitted from the fluorescence material labelling a detection object substance which is captured by a capturing body of detection target region 149, fluorescence having a small angle relative to the central axis of optical fiber 180 is incident on core 181 through film 142. The light incident on core 181 is guided to detector 160 through dichroic mirror 161 and filter 162 via through core 181. In addition, the fluorescence having a large angle relative to the central axis of optical fiber 180 is incident on core 181 and clad 182 through film 142. The light incident on core 181 is guided to detector 160 through dichroic mirror 161 and filter 162 via core 181 and clad 182.

(Effect)

As described above, in detection apparatus 100 according to the present embodiment, an end portion of optical fiber 180 on detection target region 149 side is adjacent to chip 140 (film 142), and the excitation light emitted from light source 120 is guided to chip 140 (fluorescence material) with core 181 of optical fiber 180 whereas the fluorescence emitted from the fluorescence material is guided to detector 160 with core 181 of optical fiber 180 and clad 182. Accordingly, detection apparatus 100 can detect the fluorescence emitted from the fluorescence material with high sensitivity.

[Modification]

A detection apparatus according to a modification of Embodiment 1 is different from detection apparatus 100 according to Embodiment 1 in the configuration of optical fiber 180. Therefore, the components same as those of detection apparatus 100 according to Embodiment 1 are denoted with the same reference numerals and the description thereof is omitted, and, components different from detection apparatus 100 are mainly described below.

(Configuration of Detection Apparatus)

Figure 5A:
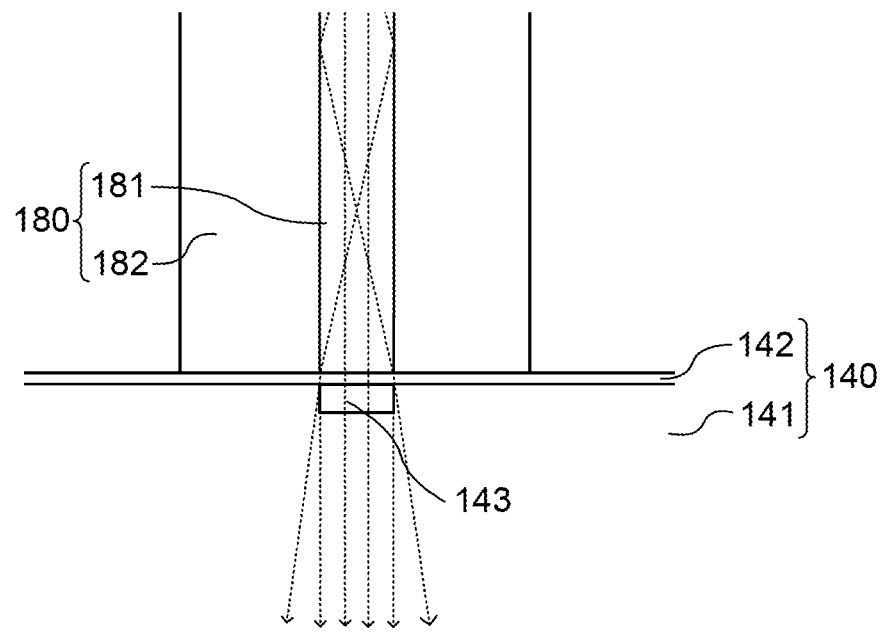
FIG. 5A illustrates light paths of excitation light of an optical fiber part of a modification of Embodiment 1.
Figure 5B:
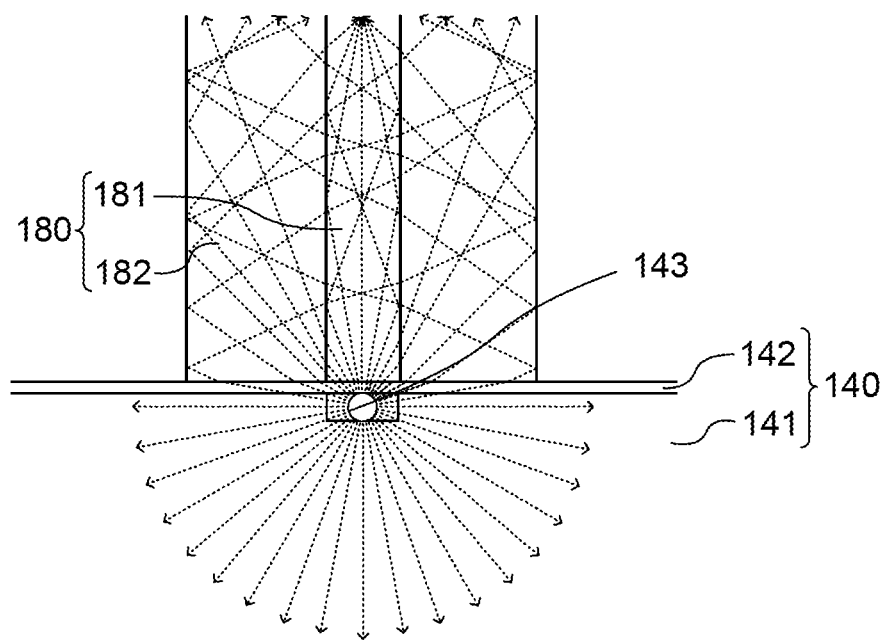
FIG. 5B illustrates light paths of fluorescence in the optical fiber part.

FIG. 5A and FIG. 5B illustrate light paths of optical fiber 180 in detection apparatus 100. FIG. 5A illustrates a part of light paths of excitation light, and FIG. 5B illustrates a part of light paths of fluorescence.

As illustrated in FIG. 5A and FIG. 5B, optical fiber 180 includes core 181 and clad 182. Core 181 has a configuration similar to that of Embodiment 1. In the present modification, it is preferable to set the thickness of clad 182 in the direction orthogonal to central axis CA to a large value as much as possible in view of efficiently causing incidence of detection light into clad 182. However, in a case where chip 140 is to be downsized, or a case where a plurality of channels 143 adjacent to each other are formed, the thickness of clad 182 is limited in view of the distance between channels 143. To be more specific, in the present modification, the thickness of clad 182 in the direction orthogonal to central axis CA is about four to five times the maximum diameter of core 181.

As illustrated in FIG. 5A, the excitation light emitted from light source 120 is reflected by dichroic mirror 161, and emitted toward chip 140 (fluorescence material) through core 181. The excitation light emitted toward chip 140 is applied to the fluorescence material disposed in the detection target region through film 142. As illustrated in FIG. 5B, in the fluorescence emitted from the fluorescence material labelling the detection object substance which is captured by the capturing body of detection target region 149, the fluorescence having a small angle relative to the central axis of optical fiber 180 is incident on core 181 through film 142. The light incident on core 181 is guided to detector 160 through dichroic mirror 161 and filter 162 via through core 181. In addition, the fluorescence having a large angle relative to the central axis of optical fiber 180 is incident on core 181 through film 142. The light incident on core 181 is guided to detector 160 through dichroic mirror 161 and filter 162 via core 181 and clad 182. Further, the fluorescence having a significantly large angle to the central axis of optical fiber 180 is incident on clad 182 through substrate 141 and film 142. The light incident on clad 182 is guided to detector 160 through dichroic mirror 161 and filter 162 via core 181 and clad 182.

(Effect)

As described above, in the detection apparatus according to the modification of Embodiment 1, the thickness of clad 182 of optical fiber 180 is large relative to the diameter of core 181 of optical fiber 180. Consequently, in the fluorescence emitted from the fluorescence material, the fluorescence having a large angle relative to the central axis of optical fiber 180 can also be guided to detector 160 (see FIG. 5A and FIG. 5B). Thus, detection sensitivity can be further increased in comparison with detection apparatus 100 of Embodiment 1.

Figure 6A:
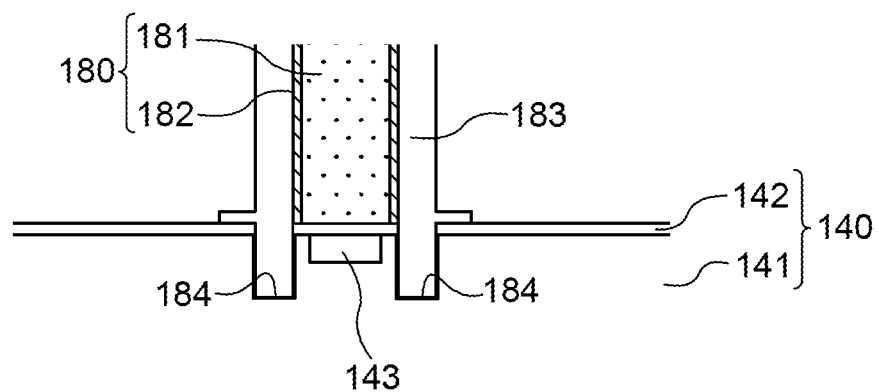
FIG. 6A and FIG. 6B are sectional views illustrating another configuration of the optical fiber.
Figure 6B:
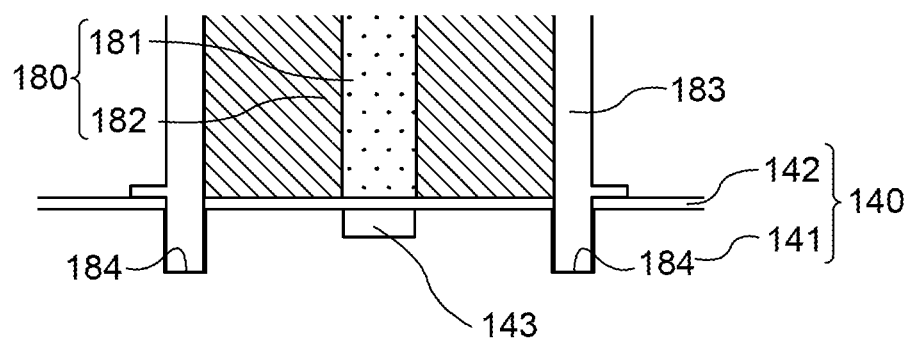

It is to be noted that, as illustrated in FIG. 6A and FIG. 6B, optical fiber 180 may be fixed to chip 140 with ferrule (connector) 183. In this case, engagement hole 184 for engaging an tip end portion of ferrule 183 is disposed in chip 140. With this configuration, optical fiber 180 can be appropriately fixed to chip 140 (detection target region 149), and as a result, ease of alignment of the optical axis of optical fiber 180 in detection target region 149 can be increased. In addition, chip 140 may be provided with a fitting part for fixing optical fiber 180 to fix optical fiber 180 to chip 140 without interposing ferrule 183 therebetween.

[Embodiment 2]

A detection apparatus according to a modification of Embodiment 2 is different from detection apparatus 100 according to Embodiment 1 in the configurations of chip 240 and optical fiber 280. Therefore, the components same as those of detection apparatus 100 according to Embodiment 1 are denoted with the same reference numerals and description thereof is omitted, and, components different from those of detection apparatus 100 are mainly described below.

(Configuration of Detection Apparatus)

Figure 7A:
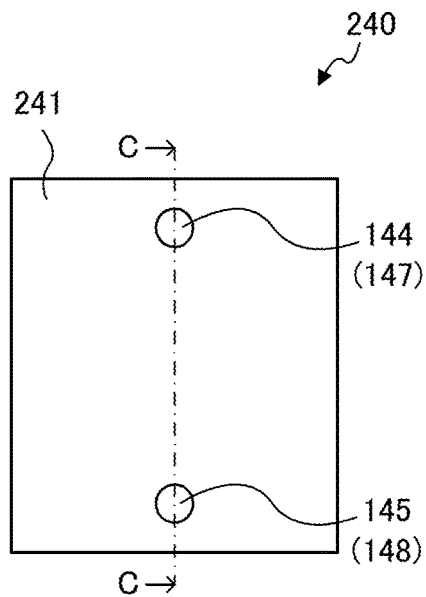
FIG. 7A to FIG. 7D illustrate a configuration of a chip according to Embodiment 2.
Figure 7B:
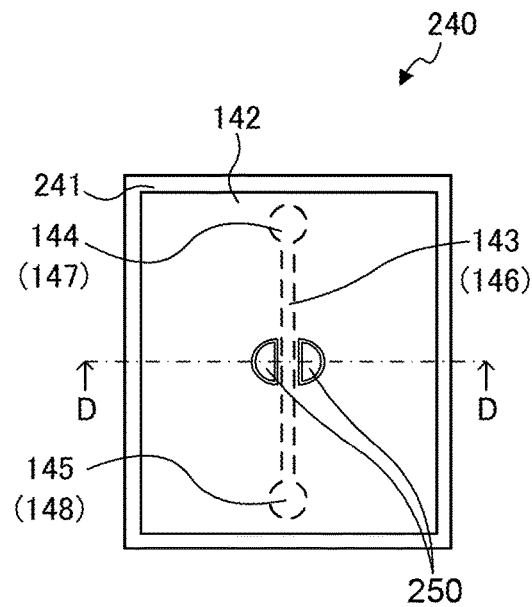
Figure 7C:
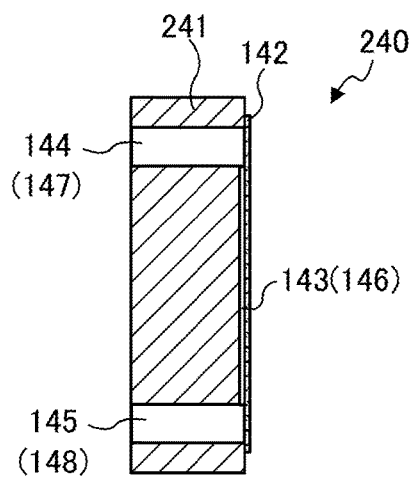
Figure 7D:
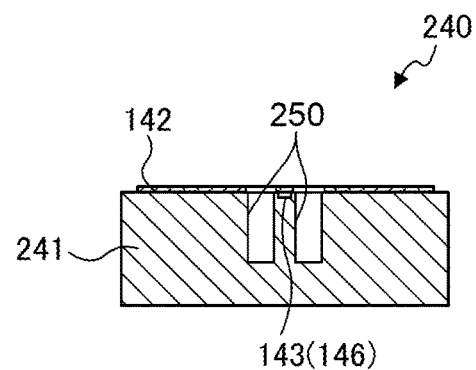
Figure 8A:
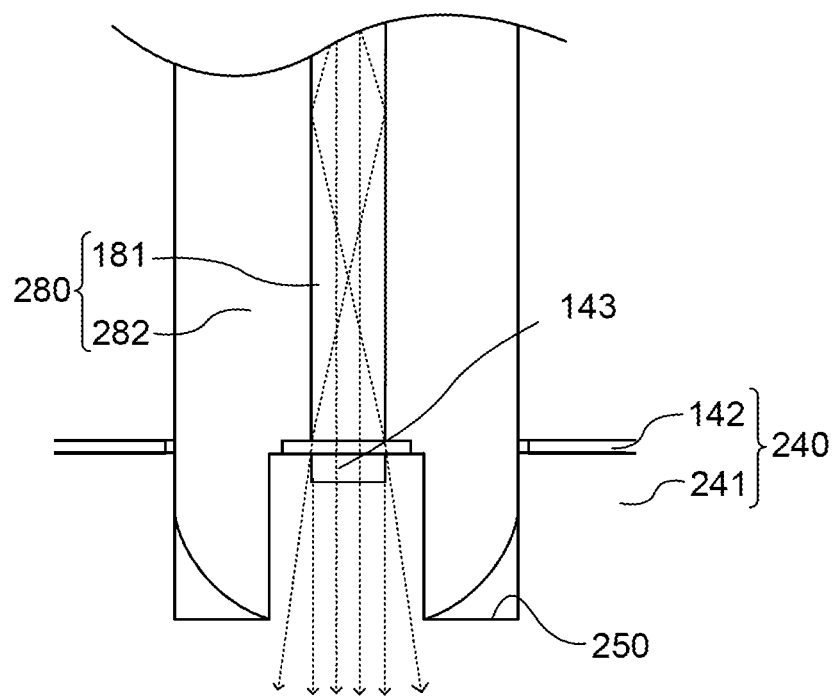
FIG. 8A illustrates light paths of excitation light in an optical fiber part according to Embodiment 2.
Figure 8B:
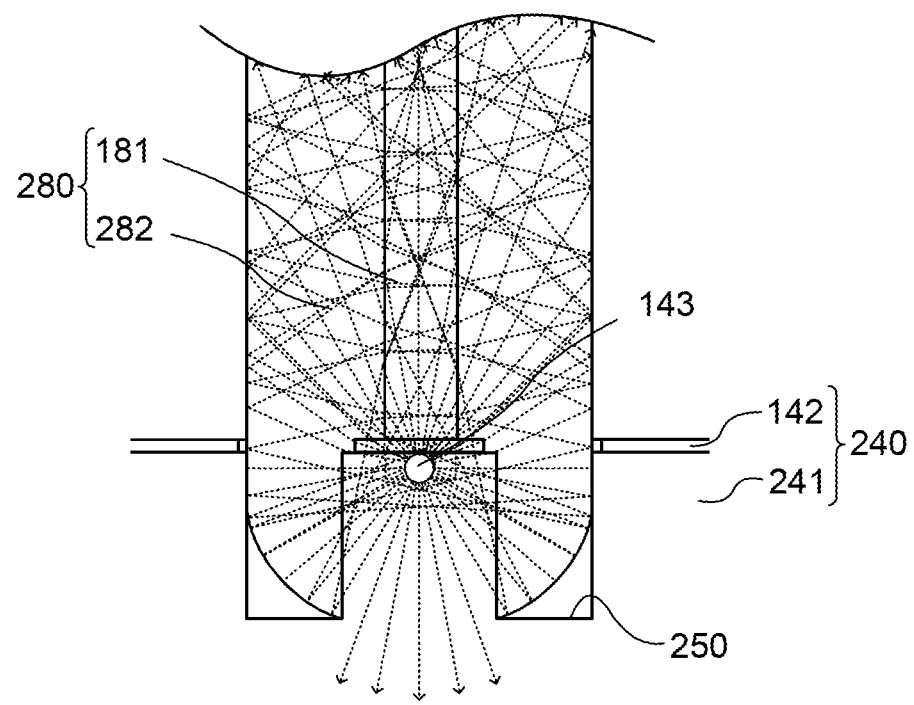
FIG. 8B illustrates light paths of fluorescence in the optical fiber part.

FIG. 7A to FIG. 7D illustrate a configuration of chip 240 according to Embodiment 2. FIG. 7A is a plan view of chip 240, FIG. 7B is a bottom view chip 240, FIG. 7C is a sectional view taken along line C-C of FIG. 7A, and FIG. 7D is a sectional view taken along line D-D of FIG. 7B. FIG. 8A and FIG. 8B illustrate light paths of optical fiber 280 in the detection apparatus. FIG. 8A illustrates a part of light paths of excitation light, and FIG. 8B illustrates a part of light paths of fluorescence.

As illustrated in FIG. 7A to FIG. 7D, chip 240 is composed of substrate 241 and film 142. Chip 240 includes two recesses 250 in addition to channel 143, sample inlet 144, and sample outlet 145.

Recesses 250 are holes for fitting an end of optical fiber 280. Recesses 250 are opposed to each other with channel 143 therebetween. The shape of recesses 250 is not limited as long as the tip end portion of optical fiber 280 can be fitted. In the present embodiment, the bottom surface is formed in a semicircular columnar shape.

As illustrated in FIG. 8A and FIG. 8B, optical fiber 280 includes core 181 and clad 282. At the end portion of optical fiber 280 on detection target region 149 side, the end of clad 282 protrudes to chip 240 (detection target region) side over the end of core 181. To be more specific, in a cross-section which includes the central axis of optical fiber 280 and which is taken along the liquid flow direction, the end of clad 282 is flush with the end surface of core 181. On the other hand, in a cross-section which includes the central axis of optical fiber 280 and is taken along a direction orthogonal to the liquid flow direction, the end of clad 282 protrudes over the end of core 181. In addition, in a cross-section taken along a direction orthogonal to the liquid flow direction, an outer peripheral surface of the tip end portion of clad 282 is a curved line protruding outward for guiding fluorescence to the end portion of optical fiber 280 on detector 160 side.

(Effect)

As described above, in the detection apparatus according to Embodiment 2, the end surface of clad 282 of optical fiber 280 protrudes to chip 240 side over the end surface of core 181. Consequently, in the fluorescence emitted from the fluorescence material, the fluorescence having a further large angle relative to the central axis of optical fiber 280 can also be guided to detector 160 (see FIG. 4B, FIG. 5B and FIG. 8B). Thus, detection sensitivity can be further increased in comparison with detection apparatus 100 of Embodiment 1.

Figure 9A:
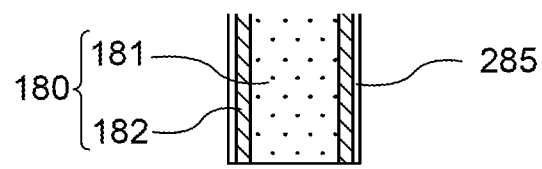
FIG. 9A to FIG. 9C are sectional views illustrating another configuration of the optical fiber.
Figure 9B:
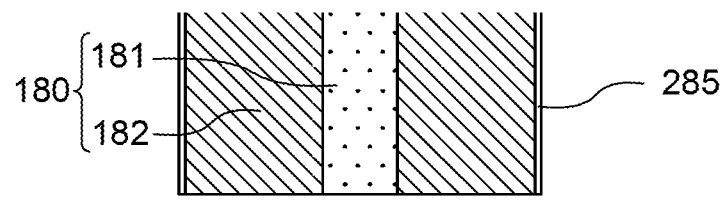
Figure 9C:
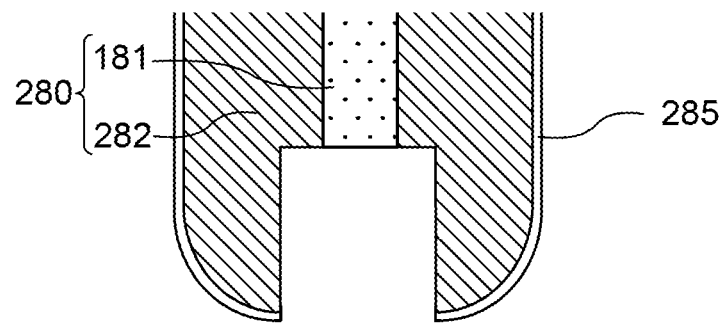

It is to be noted that as illustrated in FIG. 9A to FIG. 9C, reflection film 285 as a reflection member for reflecting the fluorescence may be formed on the outer peripheral surface of clad 182 or 282. In this case, normally, reflection film 285 is formed over the entirety of the outer peripheral surface although reflection film 285 may be formed only at a part of the outer peripheral surface. The material of reflection film 285 is not limited, and is a metal, for example. The way of forming reflection film 285 is not limited, and, for example, reflection film 285 is formed by an evaporation method. The light (fluorescence) from clad 182 or 282 side is reflected to clad 182 or 282 side by reflection film 285.

In addition, core 181 may be shorter than the end of clad 182 or 282 in a cross-section including central axis CA of optical fiber 180 or 280 and taken along the liquid flow direction such that a gap is formed between the surface of film 142 and core 181 when optical fiber 180 or 280 is fixed to chip 140 or 240. In this case, optical fiber 180 or 280 can be fixed to chip 140 or 240 without damaging the surface of film 142 with the end portion of optical fiber 180 or 280 in detection target region 149.

Further, refractive index matching agent such as matching oil may be provided in a gap between the surface of film 142 and core 181. In this case, fresnel reflection loss of detection light at an end portion of core 181 can be suppressed.

This application is entitled to and claims the benefit of Japanese Patent Application No. 2014-029475 filed on Feb. 19, 2014, the disclosure each of which including the specification, drawings and abstract is incorporated herein by reference in its entirety.

INDUSTRIAL APPLICABILITY

The detection apparatus according to the embodiments of the present invention can detect fluorescence with high sensitivity, and therefore is suitable for food tests, laboratory tests, environment tests, and the like, for example.

REFERENCE SIGNS LIST

100 Detection apparatus
120 Light source
140, 240 Chip
141, 241 Substrate
142 Film
143 Channel
144 Sample inlet
145 Sample outlet
146 Groove
147 First through hole
148 Second through hole
149 Detection target region
160 Detector
161 Dichroic mirror
162 Filter
180, 280 Optical fiber
181 Core
182, 282 Clad
183 Ferrule
184 Engagement hole
250 Recess
285 Reflection film

The invention claimed is:

1. A detection apparatus comprising:
a chip including a detection target region for detecting a detection object substance;
a light source configured to emit excitation light;
a detector configured to detect fluorescence emitted from a fluorescence material labelling the detection object substance and excited with the excitation light; and
an optical fiber including a core and a clad which covers an outer peripheral surface of the core, the optical fiber being configured to guide excitation light emitted from the light source to the detection target region, and guide fluorescence emitted from the fluorescence material to the detector, wherein:
the optical fiber is directly fixed to the chip, or fixed to the chip through a connector;
the excitation light emitted from the light source is guided in the core and reaches the detection target region of the chip;
the fluorescence emitted from the fluorescence material is guided in the core and the clad and reaches the detector; and
at an end surface of the optical fiber on a detection target region side, a tip end surface of the clad protrudes toward the detection target region side relative to a tip end surface of the core.

2. The detection apparatus according to claim 1, wherein, in a cross-section including an axis of the optical fiber, a cross-sectional width of the core falls within a range of ±10% of a cross-sectional width of the detection target region.

3. The detection apparatus according to claim 1, wherein a reflection member configured to reflect light inside the optical fiber is disposed on an outer peripheral surface of the clad.

4. The detection apparatus according to claim 1, wherein an outer peripheral surface of the tip end portion of the clad is a curved line protruding outward in a cross-section taken along the axis of the optical fiber.

5. The detection apparatus according to claim 1, wherein recesses capable of fitting the tip end portion of the clad is disposed around the object detection region of the chip.

6. The detection apparatus according to claim 5, wherein:
the detection target region is a part of a channel which is formed when a groove formed on the chip is sealed with a film; and
the recesses are opposed to each other with the channel therebetween.

7. The detection apparatus according to claim 1, wherein the optical fiber is fixed to the chip through the connector.

* * * * *